(12) United States Patent
Parida

(10) Patent No.: US 8,355,878 B2
(45) Date of Patent: Jan. 15, 2013

(54) METHOD AND SYSTEM FOR IDENTIFYING PARTIAL ORDER PATTERNS IN SEQUENCES OF DATA

(75) Inventor: Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 717 days.

(21) Appl. No.: 12/102,176

(22) Filed: Apr. 14, 2008

(65) Prior Publication Data

US 2009/0259626 A1 Oct. 15, 2009

(51) Int. Cl.
*G06F 19/00* (2011.01)
*G06F 15/00* (2006.01)
*G11C 17/00* (2006.01)

(52) U.S. Cl. .................... 702/20; 365/94; 700/1

(58) Field of Classification Search .............. None
See application file for complete search history.

(56) References Cited

U.S. PATENT DOCUMENTS

| | | | |
|---|---|---|---|
| 6,571,230 | B1 | 5/2003 | Parida |
| 6,931,418 | B1 | 8/2005 | Barnes |

OTHER PUBLICATIONS

Parida et al. (Redescription Mining: Structure Theory and Algorithms, Proceedings of AAAI, 2005, pp. 8 of 8, printed from http://arnetminer.org/dev.do?m=downloadpdf&url=http://arnetminer.org/pdf/PDFFiles/--g---g-Index1237085900111/Redescription Mining Structure Theory and Algorithms1237085921722.pdf on Mar. 13, 2011.*

Koonin et al. (Nucleic Acids Research, vol. 23, pp. 4229-4233, 1995.*

Sun et al. , Proc LSS Comput syst Bioinform Conf. Aug. 2007, vol. 6, pp. 299-310.*

\* cited by examiner

*Primary Examiner* — John S Brusca
(74) *Attorney, Agent, or Firm* — Scully, Scott, Murphy & Presser, P.C.; Anne V. Dougherty, Esq.

(57) ABSTRACT

A method and system are disclosed for identifying partial order patterns of a set of motifs in a data sequence. The method comprises the steps of obtaining the data sequence, identifying a set of motifs in the data sequence, identifying a plurality of partial orders of the motifs in the data sequence, and using the identified partial orders to identify functions of the motifs. In the preferred embodiment of the invention, the step of identifying the plurality of partial orders of the motifs includes the step of converting the identified motifs to an (n×m) incidence matrix, I, of expressions. Also, in this preferred embodiment, the step of identifying the plurality of partial orders of the motifs includes the steps of computing a partial order description of each of the expressions, and computing a redescription of each of the partial order descriptions.

19 Claims, 7 Drawing Sheets

OUTLINE OF THREE STEP PROCESS

Generic($S, j, K, flg, cP, B, E, d, dpth$)

(0.00) IF ($j \leq 0$) EXIT; IF ($d \geq dpth$) EXIT
(1.00) $I_b \leftarrow B, I_e \leftarrow E$
(2.00) FOR $L \leftarrow I_b, I_e$
(2.01)      Ancestor$_L \leftarrow$ TRUE
                                                     //$S_L[1] \leftarrow \{ i \mid I[(i \in S), j] = L \}$
(2.02)      FOR each $i \in S[1]$
(2.03)          IF $I[i,j] = L$ $S_L[1] \leftarrow S_L[1] \cup \{ i \}$
(2.04)             ELSE Ancestor$_L \leftarrow$ FALSE
(2.05)      IF ($l = 0$) $f \leftarrow F_i$ ELSE $f \leftarrow F_j$
(2.06)      $S_L[2] \leftarrow S[2] \cup \{ f \}$
(3.00) FOR $L \leftarrow I_b, I_e$          //1st and 2nd child of traversal
(3.01)      IF $|S_L[1]| \geq K$ {
(3.02)          IF $S_L[1]$ exists in $T$ as $S^p[1]$ {
(3.03)             IF (cP) $S$ is added to parent list of $S^p$
(3.04)             IF Ancestor$_L$ = TRUE {      //$S[2] \supset S^p[2]$ holds
(3.05)                 IF flg = Maximal
(3.06)                     Update $S^p[2] \leftarrow S^p[2] \cup S_L[2]$
(3.07)                 Generic($S_L, j-1, K, flg, cP, B, E, d+1, dpth$)
(3.08)             ELSE                    //$S[2] \subset S^p[2]$ HOLDS
(3.09)                 IF flg = Minimal Add $S_L$ to $T$ as $S^q$
                                                              //terminating traversal
(3.10)             } // [IF Ancestor$_L$ = TRUE]
(3.11)          ELSE //[IF $S_L[1]$ exists]
(3.12)          Add $S_L$ $T$ as $S^q$
(3.13)          IF (cP) $S$ is assigned parent of $S_L$
(3.14)          Generic($S_L, j-1, K, flg, cP, B, E, d+1, dpth$)
(3.15)      } //[IF $S_L[1]$ exists]
(3.16)      } //[IF $S_L[1] \geq K$]
(4.00) Generic($S, j-1, K, flg, cP, b, E, d, dpth$)
                                                     //3rd child of traversal

FIG. 4

$M'$ FOR $s_1 = 1234$ $s_2 = 3142$ $s_3 = 4132$

PARTIAL ORDER, $M'_1$

AUGMENTED PARTIAL ODER, $M'_2$

METHOD AND SYSTEM FOR IDENTIFYING PARTIAL ORDER PATTERNS IN SEQUENCES OF DATA

BACKGROUND OF THE INVENTION

1. Field of the Invention

This invention generally relates to data sequence processing methodologies, and more particularly, to methods and systems for identifying partial order patterns in sequences of data such as, for example, sequences of characters, character sets and real numbers.

2. Background Art

Given an input sequence of data, a "motif" is a repeating pattern, possibly interspersed with don't-care characters, that occurs in the sequence. The data could be characters or sets of characters or real values. In the first two cases, the number of motifs could potentially be exponential in the size of the input sequence, and in the third case there could be uncountably infinite number of motifs. Typically, the higher the self-similarity in the sequence, the greater is the number of motifs in the data. Motif discovery on such data, such as repeating DNA or protein sequences, is a source of concern since such data exhibits a very high degree of self-similarity (repeating patterns).

Given a body of evidence as a sequence of motifs or genes or markers, the task is to mine information from this data. A maximal boolean expression pattern gives all the motifs that describe the set of sequences. However, it is sometimes observed that the same set of motifs may be present but the sequences are endowed with different functions. A closer look reveals that the partial orders of these motifs are different for different functions.

SUMMARY OF THE INVENTION

An object of this invention is to identify partial order patterns in a group of sequences.

Another object of the present invention is to derive the minimal information required to describe the functionality of a set of data by studying the maximal patterns that the data set produces.

These and other objectives are attained with a method of and system for identifying partial order patterns of a set of motifs in a data sequence. The method comprises the steps of obtaining the data sequence, identifying a set of motifs in the data sequence, identifying a plurality of partial orders of the motifs in the data sequence, and using the identified partial orders to identify functions of the motifs.

In the preferred embodiment of the invention, the step of identifying the plurality of partial orders of the motifs includes the step of converting the identified motifs to an (n×m) incidence matrix, I, of expressions, and this may be done by using a Boolean expression to compute the expressions of the incidence matrix. In addition, in this preferred embodiment, the step of identifying the plurality of partial orders of the motifs includes the further steps of computing a partial order description of each of said expressions, and computing a redescription of each of said partial order descriptions.

The preferred embodiment of the invention captures the player motifs along with their partial orders. Also, this embodiment of the invention derives the minimal information required to describe the functionality of a data set by studying all the other maximal patterns that the given data set produces.

Further benefits and advantages of this invention will become apparent from a consideration of the following detailed description, given with reference to the accompanying drawings, which specify and show preferred embodiments of the invention.

BRIEF DESCRIPTION OF THE DRAWINGS

FIG. 4 shows a generic biclustering algorithm that is capable of computing both maximal and minimal biclusters.

DETAILED DESCRIPTION OF THE PREFERRED EMBODIMENTS

Figure 1:
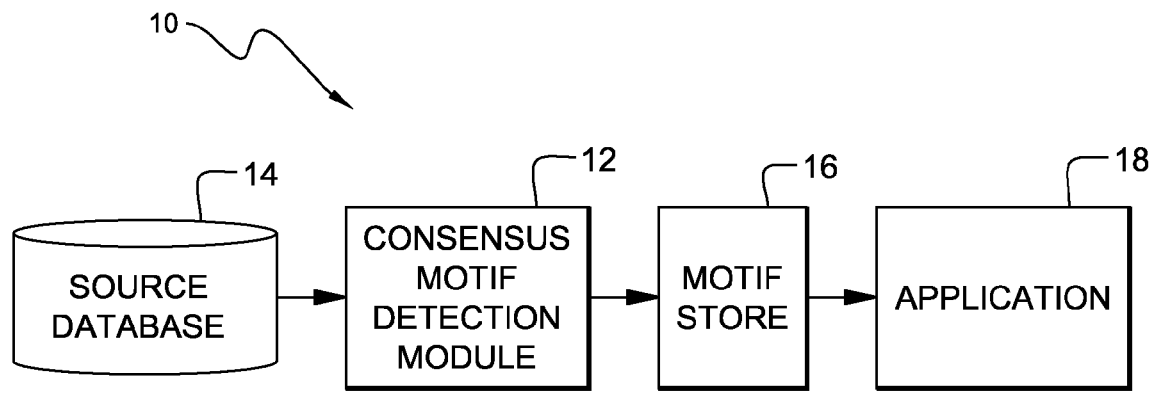
FIG. 1 is a block diagram illustrating a system for identifying partial order patterns according to one embodiment of the present invention.

Referring initially to FIG. 1, a block diagram of a motif detecting system according to an embodiment of the present invention is shown. The illustrative system 10 includes a motif detection module 12, a source sequence database 14 and a motif store 16. Also shown is an application 18, which is not necessarily part of the system, but which utilizes one or more of the motifs stored in store 16. Generally, the module 12 employs a pattern discovery or detection algorithm, to be explained in detail below, in order to discover consensus motifs from data input from the source database 14. It is to be appreciated that the source database comprises data sequences from which repeating data patterns are discovered for use by one or more applications such as, for example, data mining, clustering or matching applications. The data sequences in the database may, for example, be in the form of sequences of discrete characters from a fixed character alphabet, sets of discrete characters from a fixed character alphabet, or sequences/sets of real numbers.

It is to be appreciated that another application, which may implement the motif detection methodologies of the invention, is deoxyribonucleic acid (DNA) or protein sequence homology detection. In such an application, a probe protein sequence may be submitted to a search engine system implementing the invention in order to check for k occurrences of the probe sequence in the database of protein sequences.

Figure 2:
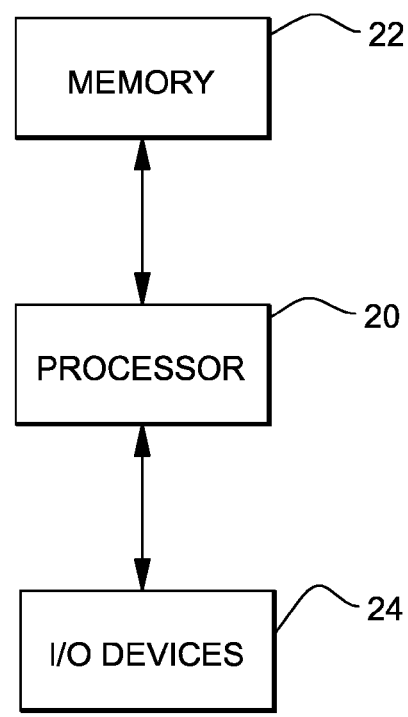
FIG. 2 is a block diagram illustrating a hardware implementation of a partial order identification system according to one embodiment of the present invention.

FIG. 2 is a block diagram of an exemplary hardware implementation of the system 10 of FIG. 1. As shown, the system 10 may be implemented in accordance with a processor 20 a memory 22 and I/O devices 24. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, a fixed memory device (e.g., hard drive), a removable memory device (e.g., diskette), flash memory, etc.

In addition, the term "input/output devices" or "I/O devices" as used herein is intended to include, for example, one or more input devices, e.g., keyboard, for entering sequences and/or other data to the processing unit, and/or one or more output devices, e.g., CRT display and/or printer, for presenting discovery results and/or other results associated with the processing unit. It is also to be understood that the term "processor" may refer to more than one processing device and that various elements associated with a processing device may be shared by other processing devices. Accordingly, software components including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

It is to be appreciated that, in an alternative embodiment, the invention may be implemented in a network-based implementation. That is the user may submit source data sequences (in lieu of a separately stored source database 14) at a remote client computer system, while the detection module 12 resides and is executed on a server computer system in communications with the client via a network such as, for example, the Internet. The network could alternatively be a private network and/or a local network. Thus, a user operating remotely on his client computer system, e.g., a personal computer, laptop and/or some other type of personal processing device, enters data sequences through application software running on the computer system, e.g., web browsing software and/or a graphical user interface associated with the system.

The sequences are passed over the network, in a conventional manner, and processed by server. The server receives the sequences and executes the methodologies of the invention in order to discover and/or generate motifs. The server then returns some or all of the results to the client via the network. It is to be understood that the server may include more than one computer system. That is, one or more of the elements in FIG. 2 may reside on and be executed by their own computer system, e.g., with its own processor, memory and I/O devices.

Given a general description of the elements of the partial order identification system of the invention and various exemplary hardware implementations, the various inventive methodologies will now be explained in detail.

We begin with a simple example that uses partial order descriptions.

Example 1 Let the input be a (ordered) collection of 10 sequences on some finite vocabulary F. In practice this alphabet is a collection of motifs in the sequences. Consider the following example (each $f_i \in F$) where a relevant segment of each sequence is shown.

(1) ... $f_1 f_2 f_3 f_4 f_5 f_6 f_8 f_9 f_{10} f_{11} f_{12}$ ...
(2) ... $f_{12} f_1 f_3 f_2 f_4 f_5 f_6 f_7 f_8 f_9 f_{10} f_{11}$ ...
(3) ... $f_{12} f_1 f_3 f_2 f_{13} f_5 f_4 f_7 f_6 f_9 f_{10} f_{11}$ ...
(4) ... $f_{12} f_1 f_3 f_2 f_5 f_4 f_6 f_8 f_{10} f_9 f_{11}$ ...
(5) ... $f_1 f_4 f_3 f_2 f_5 f_6 f_7 f_8 f_9 f_{10} f_{11} f_{12} f_{13}$ ...
(6) ... $f_{13} f_1 f_3 f_2 f_5 f_4 f_6 f_8 f_9 f_{11} f_{10}$ ...
(7) ... $f_4 f_{12} f_1 f_3 f_2 f_7 f_6 f_8 f_{10} f_9 f_{11} f_5$ ...
(8) ... $f_4 f_1 f_3 f_2 f_5 f_6 f_7 f_8 f_9 f_{10} f_{11} f_{13}$ ...
(9) ... $f_{13} f_1 f_{12} f_3 f_2 f_5 f_4 f_7 f_6 f_{10} f_9 f_{11}$ ...
(10) ... $f_{12} f_1 f_2 f_5 f_4 f_7 f_6 f_8 f_{10} f_{11} f_9 f_{14}$ ...

An ordered description d, with $O(d)=\{1, 2, 4, 6\}$, is written as follows:

$$d = ((f_1, f_2, f_3) \to ((f_4, f_5, f_6)^\wedge (f_7 V f_8)) \to (f_9, f_{10}))$$

This is to be interpreted as follows: there are three common segments, X, Y, Z organized as X followed by Y followed by Z in the rows given by O(d). Specifically, X is a collection of features $f_1, f_2, f_3$; $Y = Y_1^\wedge Y_2$, where $Y_1$ is a collection of features, $f_4, f_5, f_6$ and $Y_2$ is a collection of features, $f_7, f_8$; Z is features $f_9$ and $f_{10}$.

Also $\Pi(d) = \{f_1, f_2, f_3, f_4, f_5, f_6, f_7, f_8, f_9, f_{10}\}$: there may be other intervening features.

Forms of Descriptions

Care needs to be exercised for a description as general as this. Firstly, it should be non-trivial; we use the following definition.

Definition 1 (well-defined description) A form of description is non-trivial if both the conditions hold: (1) if there exists a collection of objects in some input that does not admit a valid description and (2) the description is unique (up to equivalence).

To make the ordered description well defined, e uses a restriction on the form of boolean expressions: we choose them to be in monotone conjunctive normal form (CNF). Note that any monotone expression can be expressed in the monotone CNF form.

Figure 3:
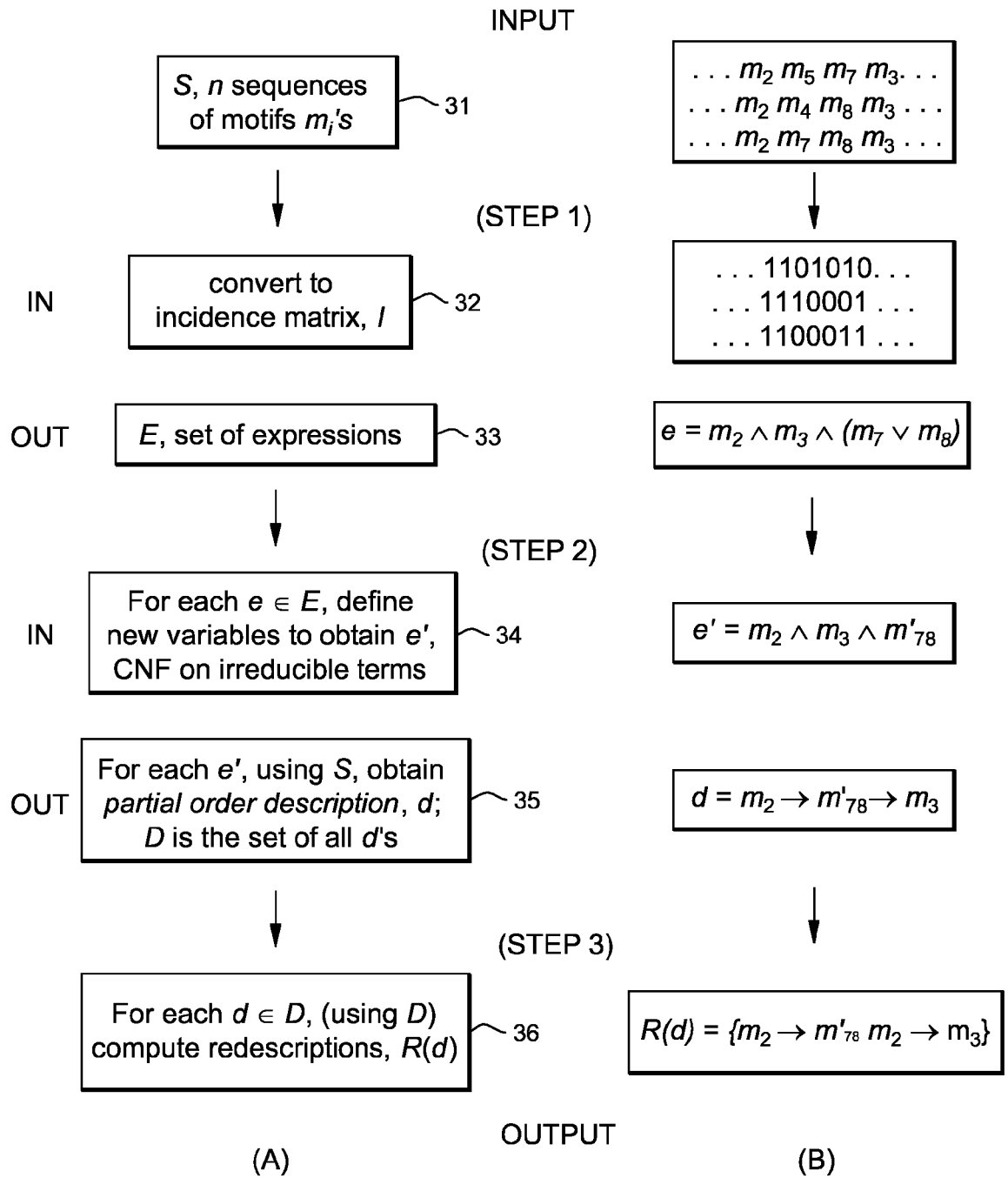
FIG. 3 outlines a three-step process for identifying partial order patterns in accordance with a preferred embodiment of the present invention.

The overall process of a preferred embodiment of the invention is described in FIG. 3. The input, represented at 31, to the overall process is shown in the top row and the rightmost column shows a simple running example. Step (1), represented at 32 and 33, computes the descriptions as Boolean expressions (using AND, OR etc.). Step (2), represented at 34 and 35, computes the partial order description of each expression using the order information in S. Step (3), represented at 36, computes the redescriptions of each descriptor using all the descriptions of the previous step: this is the output to the overall process. Each of these steps is discussed in detail below.

The given input of n sequences, S on a set of motifs, F, is converted to an (n×m) incidence matrix, I, as follows:

$$I[i, j] = \begin{cases} 1 & \text{if motif } m_j \text{ occurs in sequence } s_i \in S \\ 0 & \text{otherwise.} \end{cases}$$

The descriptors at this stage are Boolean expressions. To avoid confusion with descriptors discussed below in connection with Step (3), we will refer to these descriptors as expressions.

Definition 2 (expression e, features $\Pi(e)$, objects $O(e)$) e is a boolean expression on a set of motifs $V \subset F$. Given e, we denote the set of motifs involved in e by $\Pi(e)$ and the set of sequences it represents by $O(e)$.

Two expressions (descriptors) $e_1$ and $e_2$ defined over (resp.) $V_1$ and $V_2$ are distinct (denoted as $e_1 \neq e_2$), if one of the following holds: (1) $V_1 \neq V_2$, or (2) there exists some input I for which $O(e_1) \neq O(e_2)$. Notice that this condition rules out tautologies. For example, the descriptors $m_1 \cap m_4$ and $m_1 - (m_1 - m_4)$ are not distinct.

From Biclusters to Expressions

Given I, a bicluster is a non-empty collection of rows O and a non-empty collection of columns F such that for a fixed $j \in F$, $I[i][j] = c_j$ for a constant $c_j$ and for each $i \in O$ and there does not exist $i' \notin O$ with $I[i][j] = c_j$ for each $j \in F$.

The bicluster is maximal (or also called a closed itemset (see, M. J. Zaki, "Mining Non-Redundant Association Rules", Data Mining and Knowledge Discovery, Vol. 9(3): 223-248, 2004)) if there does not exist $j' \notin F$ with $I[i][j'] = c'_j$ for each $i \in O$ and some fixed $c'_j$. These conditions define the 'constant columns' type of biclusters (see, S. C. Madeira and A. L. Oliveira, "Biclustering Algorithms for Biological Data Analysis: A Survey", IEEE/ACM Transactions on Computational Biology and Bioinformatics, Vol. 1(1): 24-45, January 2004) for different flavors of biclusters used in the bioinformatics community.

The bicluster is minimal if for each $j \in F$, the collection of rows O and the collection of columns $F \setminus \{j\}$ is no longer a bicluster.

A generic biclustering algorithm is shown in FIG. 4, which is capable of computing both maximal and minimal biclusters. This is a biclustering algorithm that multiplexes three tasks (1) computing minimal biclusters (2) computing maximal biclusters and (3) generating the connectivity structure (partial order) of the biclusters. In detail, the algorithm can be understood as follows. For this description, assumes that depth dpth is set to (m+1), cP is set to FALSE, B and E are each set to 1. The algorithm systematically generates and maintains S, a polymorphic array of (two) sets where S [1] is a set of row numbers and S [2] is a set of column labels which are to be interpreted as an expression that is a conjunction of these column labels. Depending on how the algorithm is invoked, S will either represent a maximal or a minimal bicluster.

A maximal bicluster S is such that no other term can be added to S[2] without changing the size of S[1]. A minimal bicluster S is such that no other term can be removed from S[2] without changing the size of S [1]. Notice that when computing maximal biclusters, S [2] will be a single set but could possibly be a collection of sets when computing minimal bicluster. Given I and a quorum (support) K, the maximal or minimal biclusters are computed recursively by ordered search. The algorithm uses a data structure T, such as a tree, to store the sets S[1] and S[2] computed in lines (2.03) and (2.06) of FIG. 4, respectively, so that the query of line (3.02) can be answered in log n time. The correctness of the algorithm is based on the following lemma, which is easily verified.

Lemma 1 Let $\overline{S}$ be defined as follows: (1) $\overline{S}[1]=\{i | i \notin S[1]\}$ and (2) $\overline{S}[2]=\{\bar{f} | f \notin S[2]\}$. S is in minimal disjunction form if and only if $\overline{S}$ is in minimal conjunction form.

The depth parameter dpth is used to terminate the call when the required amounts of factors (columns) in the bicluster have been collected. The cP parameter is used to compute the connectivity in the partial order of the O(−) sets. When B is set to 0, then the negation of each column is used, when E is set to 1, the column is used as is, hence when B=E=1, then no column is negated and when B=E=0, each column is negated.

Time Complexity. Here we give the worst-case analysis of the Generic algorithm. Recall that the input incidence matrix I has n rows and m columns. Let C be all the biclusters computed. In the case of maximal biclusters, the time taken by this algorithm is O(L log n+mn) where $L = \Sigma_{c \in C} |c|$. In the case of minimal biclusters, the time taken by this algorithm is O(|C| log n+mn). Also, in each of the cases, Generic is invoked only a constant number ($\leq 2$) of times.

(Step 2) Partial Orders

We first give a brief introduction to partial orders and the related terminology. Given a finite alphabet $\Sigma$, M a binary relation (a subset of the Cartesian product of $\Sigma$) is a partial order if it is reflexive, antisymmetric and transitive. For any pair $\sigma_1, \sigma_2 \in \Sigma$, $\sigma_1 \leq \sigma_2$ if and only if $(\sigma_1, \sigma_2) \in M$ (thus $(\sigma_1, \sigma_2) \notin M$ if and only if $\sigma_1 \not< \sigma_2$).

A sequence s, on $\Sigma$, is compatible with M, if for no pair $\sigma_2$ preceding $\sigma_1$ in s, $\sigma_1 \leq \sigma_2$ holds. In other words, the order of the elements in s does not violate the precedence order encoded by M. A compatible s is also called an extension of M. s is a complete extension of M, if s contains all the elements of the alphabet $\Sigma$ that M is defined on. For convenience, we will say $s \in M$, if and only if s is a complete extension of M.

M can be represented by a directed graph $G(\Sigma, E)$ where $(\sigma_1, \sigma_2) \in E$, if and only if $\sigma_1 \leq \sigma_2$. Since M is antisymmetric, it is easy to see that this graph is acyclic. A directed acyclic graph is called a DAG. If E' is the smallest set of edges (on $\Sigma$) is such that when $\sigma_1 \leq \sigma_2$, there is a path from $\sigma_1$ to $\sigma_2$ in $G(\Sigma, E')$, is called the transitive reduction of M. The following can be easily verified and is used in the design of the algorithm to compute M'.

Lemma 2 Let M' ($\Sigma$, E') be the transitive reduction of a partial order M($\Sigma$,E). For any pair, $\sigma_1, \sigma_2 \in \Sigma$, if there is a directed path of length larger than 1, from $\sigma_1$ to $\sigma_2$ in M($\Sigma$,E), then $(\sigma_1, \sigma_2) \notin E'$.

If the directed edge $(\sigma_1, \sigma_2) \in E'$, then $\sigma_1$ is called the parent of $\sigma_2$. Similarly, $\sigma_2$ is called the child of $\sigma_1$. If there is a directed path from $\sigma_1$ to $\sigma_2$, then $\sigma_2$ is called a descendant of $\sigma_1$. In the remainder of the discussion, the transitive reduction of a partial order M will be denoted by the DAG M' ($\Sigma$, E').

Maximal Partial Order Problem

It is easy to see $s \in M(\Sigma, \phi)$ for any sequence s on $\Sigma$. Also if $s \in M'(\Sigma, E)$, then $s \in M(\Sigma, E'')$ for any $E'' \subset E$. Thus it is natural to talk about a maximal partial order, i.e., the largest E, which gives the transitive reduction of the partial order. We identify the following problem for our scenario.

Problem 1 Given sequences S, a set of sequences $s_i$, $1 \leq i \leq m$, of length $n=|\Sigma|$ each and defined on $\Sigma$, the task is to construct a maximal partial order MS'($\Sigma$, E') such $s_i \in M'(\Sigma, E')$, $1 \leq i \leq m$ Here maximality implies that if for any pair $\sigma_1$ precedes $\sigma_2$ in all the given m sequences, then $(\sigma_1, \sigma_2) \in M'$ must hold ($\sigma_2$ must be a descendent of $\sigma_1$ in M' ($\Sigma$, E')). The following is easy to verify.

Lemma 3 Given S, the maximal partial order DAG M'$_S$($\Sigma$, E') is unique.

In the discussion below, to avoid clutter, we denote M'$_S$($\Sigma$, E') by M'($\Sigma$, E') or simply M' with S and $\Sigma$ assumed implicitly.

Algorithm. A straightforward approach to the problem is to collect all pairs $(\sigma_1, \sigma_2)$ such that $\sigma_1$ precedes $\sigma_2$ in all sequences $s_i \in S$ and then construct a (transitive reduction) DAG from this. An incremental algorithm has the advantage that given $M_S$, if S is further augmented M' does not have to be recomputed from scratch.

Figure 6:
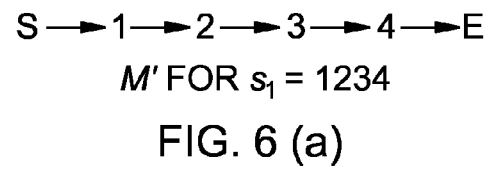
FIGS. 6a, 6b and 6c show the incremental construction of a maximal partial order
Figure 6:
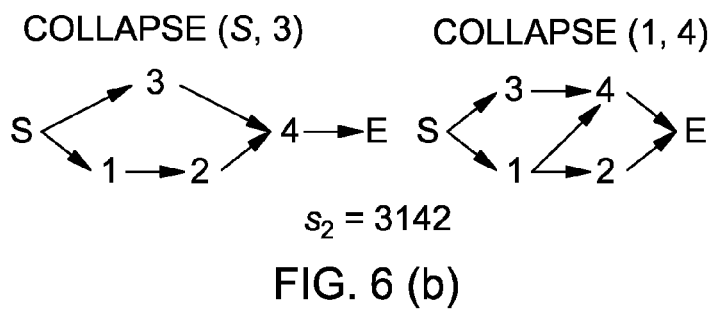
Figure 6:
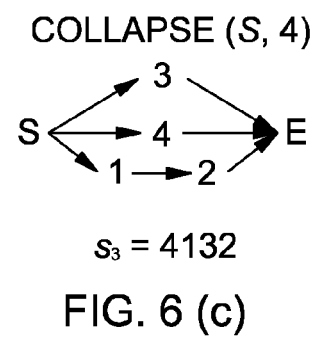

We give a simple incremental algorithm to solve the problem. For convenience, each $s_i$ is padded with a start character $S \notin \Sigma$ and an end character $E \notin \Sigma$. This also ensures the two following properties: (1) The resulting DAG M' has exactly one connected component, and (2) The only vertex in M' with no incoming edges is S and the only vertex with no outgoing edges is E. FIG. 6 shows an incremental construction of maximal partial order, M', such that $s_1$, $s_2$ and $s_3$ are compatible with M'. (a) Using only $s_1$. (b) Adding on $s_2$. (c) Adding on $s_3$.

Without loss of generality, let $s_1 = \sigma_1 \sigma_2 \sigma_3 \ldots \sigma_n$. We start with $s_1$ and construct its maximal partial order M' ($\Sigma$, E') as shown which is a "chain" as shown in FIG. 6(a). It is easy to see that this structure is maximal and is the transitive reduction of the partial order M where $s_1 \in M$. The edges E' are stored in an n×n incidence matrix E as follows:

$$E[j_1, j_2] = \begin{cases} -1 & \text{if } (j_2 < j_1) \\ (j_2 - j_1) & \text{otherwise} \end{cases}$$

Thus if $E[j_1, j_2] = (k \neq -1)$, then the length of the shortest path from vertex $\sigma_{j1}$ to $\sigma_{j2}$ in M' is k. Notice that the DAG (illustrated in the figures) is encoded in the data structure E, which the algorithm uses.

Continuing the example of FIG. 6(a), $s_2$ is read from left-to-right and the DAG is simultaneously traversed. Whenever the sequence fails the partial order DAG, the DAG is modified as follows.

Definition 3 (Collapse($\sigma_i, \sigma_j$)) Given a partial order M with $((\sigma_i, \sigma_j) \in M$. This operation collapses the path of length>1 from $\sigma_i$ to $\sigma_j$ to 1, maintaining all its other connectivity information to produce partial order M'.

Figure 5:
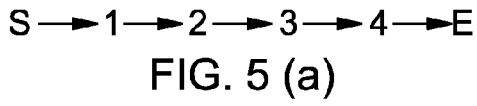
FIGS. 5a-5d illustrate the steps involved in a Collapse procedure that is used in the preferred embodiment of the present invention.
Figure 5B:
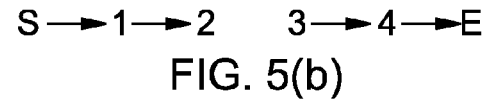
Figure 5C:
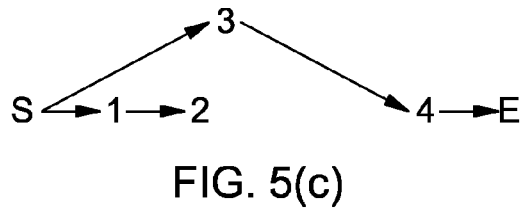
Figure 5D:
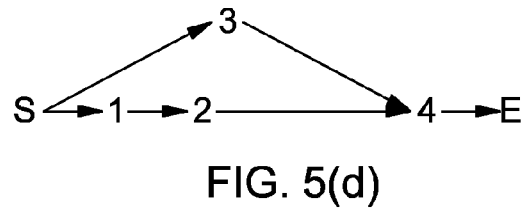

The only operation allowed on the DAG is Collapse( ). All the affected entries in E are appropriately modified. FIG. 5 illustrates the sub-steps involved in the process. The details are apparent to those of ordinary skill in the art and are omitted to avoid clutter.

FIG. 6(b) shows the two modifications to the DAG through the Collapse( ) routine while processing $s_2$ and FIG. 6(c) shows the modifications while processing $s_3$ and the final partial order DAG.

This algorithm takes $O(n^2)$ space and $O(n^2 m)$ time.

Handling Excess with PQ Structures

Let A(M) be the set of all complete extensions $s \in M$. It is clear that the partial order captures some but not all the subtle ordering information in the data and the maximal partial order $M'(\Sigma, E')$ of S is such that $A(M'(\Sigma, E')) \supseteq S$. The gap, $A(M'(\Sigma, E'))\setminus S$ is termed excess. The next task is to provide a scheme to reduce excess.

We provide a solution by augmenting $\Sigma$ with $O(|\Sigma|)$ characters in the maximal partial order DAG M'. Let this new set be $\Sigma'$. A complete extension s' on $(\Sigma \cup \Sigma')$ is converted to s on $\Sigma$ by simply removing all the $\sigma' \in \Sigma'$.

Example 2 Let S={abcdegf, bacedfg, acbdefg, edgfabc, degfbac}. It is easy to see that the maximal partial order is $M'_1$ shown in FIG. 7. In $M'_2$, the alphabet is augmented with $\{S_1, E_1, S_2, E_2, S_3, E_3\}$ to obtain a tighter description of S.

Figure 7A:
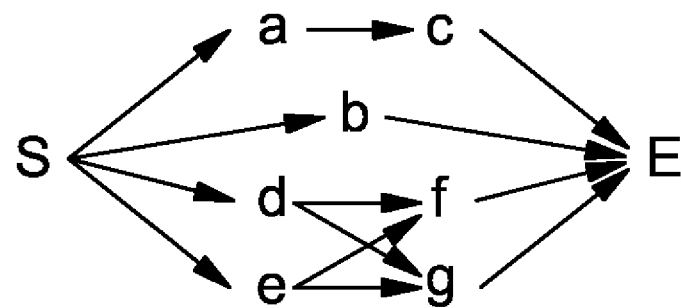
FIGS. 7a and 7b show a partial order and an augmented partial order for a given cluster of data.

The boxed elements in FIG. 7 are clusters that always appear together in S. Our scheme exploits this property to reduce excess. We use the systematic representation of these recursive clusters as PQ structures.

We begin by a brief study of clusters. Each cluster is a set of characters from $\Sigma$. Again, we must use the natural notion of maximality of clusters. Given a sequence s, a cluster c is maximal if there exists no cluster c' with $c' \subset c$ and each occurrence of c' in s is covered by an occurrence of c with the number of occurrences being the same for c and c'. The order notation for c is obtained by using a '-' between two non-maximal clusters of size one or more to denote that these clusters appear as immediate neighbors and using a '^' otherwise.

This recursive (order) notation of clusters is also naturally encoded by a data structure called the PQ tree, (See, Booth K. and Leukar G., "Testing for the consecutive ones property, interval graphs, and graph planarity using pq-tree algorithms", Journal of Computer and System Sciences, 13:335-379, 1976). The equivalence of this order notation to a PQ structure, $T_c$, along with efficient algorithms is discussed in "Using pq trees for comparative genomics", In Proc. of the Symp. on Comp. Pattern Matching, Volume 3537 of Lecture Notes in Computer Science, Pages 128-143; Springer-Verlag, 2005 (Landau, Parida, and Weimann). A PQ tree is a rooted tree whose internal nodes are of two types: P and Q. The children of a P-node occur in no particular order while those of a Q-node appear in a left to right or right to left order. We designate a P-node by a circle and a Q-node by a rectangle. The leaves of $T_c$ are labeled bijectively by the elements of c.

The frontier of $T_c$, denoted by $Fr(T_c)$, is the permutation of the elements of c obtained by reading the labels of the leaves from left to right. Two PQ trees $T_c$ and $T_c'$ are equivalent, denoted $T_c \equiv T_c'$, if one can be obtained from the other by applying a sequence of the following transformation rules: (1) Arbitrarily permute the children of a P-node, and (2) Reverse the children of a Q-node. $C(T_c)$ is defined as follows: $C(T_c) = \{Fr(T_c') | T_c' \equiv T_c\}$. An oriented PQ tree is a tree where all the Q nodes are oriented (in left-to-right or right-to-left order).

Given S, the minimal consensus PQ Tree is a structure that captures all the common clusters that appear in each $s \in S$. A linear time algorithm, $O(|S| |\Sigma|)$, to compute this tree is discussed in the above-mentioned "Using pq trees for comparative genomics", In Proc. of the Symp. on Comp. Pattern Matching, Volume 3537 of Lecture Notes in Computer Science, Pages 128-143; Springer-Verlag, 2005, (Landau, Parida and Weimann). We make a modification in the algorithm to give oriented PQ trees.

Returning to the discussion of partial orders, the number of augmented alphabet pairs $S_k, E_k, 1 \leq k \leq K$, in the augmented DAG correspond to the number of internal nodes in a PQ tree. Since this number is bounded by n in the tree, $K \leq n$, and thus $|\Sigma'| \leq 2n$. To summarize, given S, our scheme works as follows: (1) We first construct the minimal consensus oriented PQ tree T of S. (2) For each internal node we construct an instance of Problem 1 and construct the maximal partial order. (3) Using the PQ structure of step (1) we combine all the maximal partial order DAGs of (step 2), with augmented characters $S_k, E_k$ for each to obtain the augmented maximal partial order.

Figure 7B:
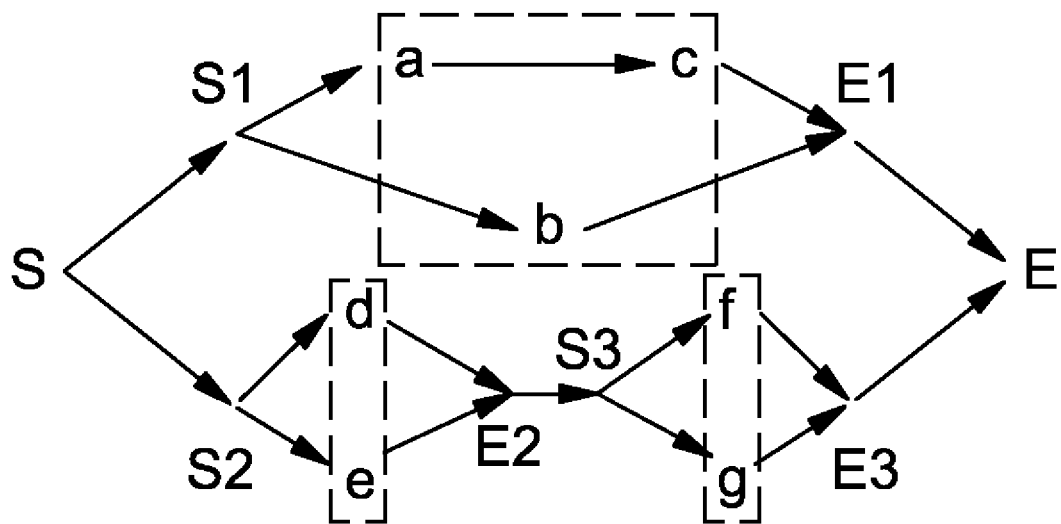
Figure 8A:
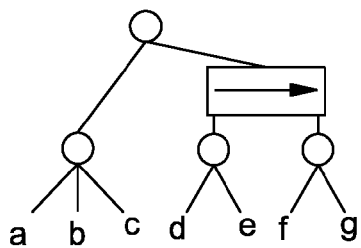
FIGS. 8a and 8b illustrate the steps taken to form the augmented partial order shown in FIG. 7b.
Figure 8B:
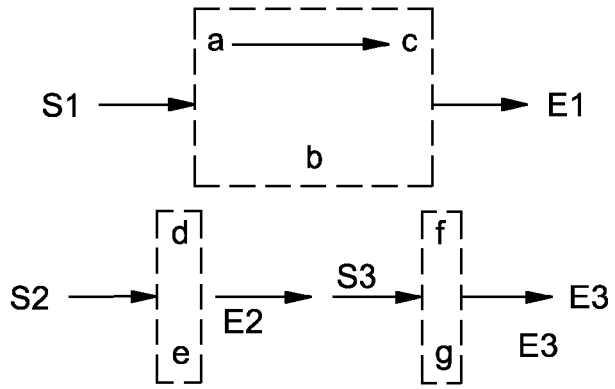

FIG. 8 shows the steps on the data of Example 2. (a) shows the minimal consensus oriented PQ tree for the input data. Then the P nodes are arranged in parallel and the Q nodes are arranged serially as shown in FIG. 8(b). For each cluster, the partial order problem is solved and the resulting DAG is shown in FIG. 7(b).

We also impose the following constraint on the complete extensions of an augmented partial order:

Definition 4 (nested complete extensions) A complete extension of a partial order augmented using oPQ structure T, is nested, if and only if each pair $S_k$ and $E_k$ is nested such that the elements between $S_k$ and $E_k$ belong to a single cluster (descendants of an internal node of T) defined by T.

Consider the augmented DAG of FIG. 7(b), which is augmented by the oPQ tree of FIG. 8(a). The complete extension $s'_1 = SS_1 acbE_1 S_2 edE_2 S_3 fgE_3 E$, is nested where as $s'_2 = SS_1 acS_2 ebE_1 dE_2 S_3 fgE_3 E$, $s'_3 = SS_1 acS_2 edE_2 bE_1 S_3 fgE_3 E$ are not. In $s'_2$ the pairs $S_k, E_k$ are not nested. In $s'_3$, although the $S_k, E_k$ pairs are nested, they do not reflect the clusters of oPQ tree of FIG. 8(a).

Comparison with Manilla. They restrict their partial orders to have an MVSP (minimal vertex series-parallel) DAG. Their aim is to count the size of A(M) (number of complete extensions of M) since they are looking for a probabilistic model of generator. We assume no restrictions on the partial order DAG.

(Step 3) Minimal Descriptions

Generally speaking, given a description d on a data S, redescription of d is yet another description d' on S such that $O(d) = O(d')$. If d' is in a simpler form, it is of interest. Note that redescriptions are always with respect to a given data set S.

Redescriptions can be formally defined, once a partial order notion is identified in the descriptions.

In the last section, M' was a (transitive reduction) partial order defined on $\Sigma$. Here we term the (transitive reduction)

partial order of a description d as $M_d$ and the feature set of $\Pi(d)=\Sigma$. Let $C(M_d)$ be the set of all nested complete extensions of $M_d$.

Given $x=f_1 f_2 \ldots f_l$, $x'=f_{i1} f_{i2} \ldots f_{ik}$ is a subsequence of x if $i_1 < i_2 < \ldots < i_k$ and $k \leq l$. In the following we will use the partial order description d interchangeably with $M_d$.

Definition 5 (Rst(d, X)) Given a partial order description $M_d$ and some $X \subset \Pi(d)$, the restriction of d to X denoted as Rst(d, X) is the partial order description d' with $\Sigma(d')=X$ and each $x' \in C(M_d')$, is a subsequence of some $x \in C(M_d)$.

Definition 6 ($d_1 \leq d_2$, $M_{d1 \leq Md2}$) $M_{d1} \leq M_{d2}$ if and only if (1) $\Pi(d_1) \subset (d_2)$, and, $C(M_{d1}) \subset C(M_{d'2})$ where $d'_2 = Rst(d_2, \Pi(d_1))$. $\overline{d_1} \leq d_2$ if and only if $\overline{M_{d1}} \leq M_{d2}$.

Next, we modify the definition of relaxation in "Redescriptions: Structure Algorithms", Proceedings of AAAI, pages 837-844, 2005 (Parida, et al.) to fit our current scenario with partial order descriptions.

Definition 7 (relaxation X(d) of d) Given d and d, d' is a relaxation of d, if and only if $(d' \leq d)$. The collection of all the relaxations of d is denoted by X(d).

It is easy to verify the following:

Lemma 4 (1) Relaxation is reflexive, anti-symmetric, and transitive: it induces a partial order on a collection of descriptors. (2) For each $d_2 \in X(d_1)$, $O(d_2) \supset O(d_1)$.

Figure 9:
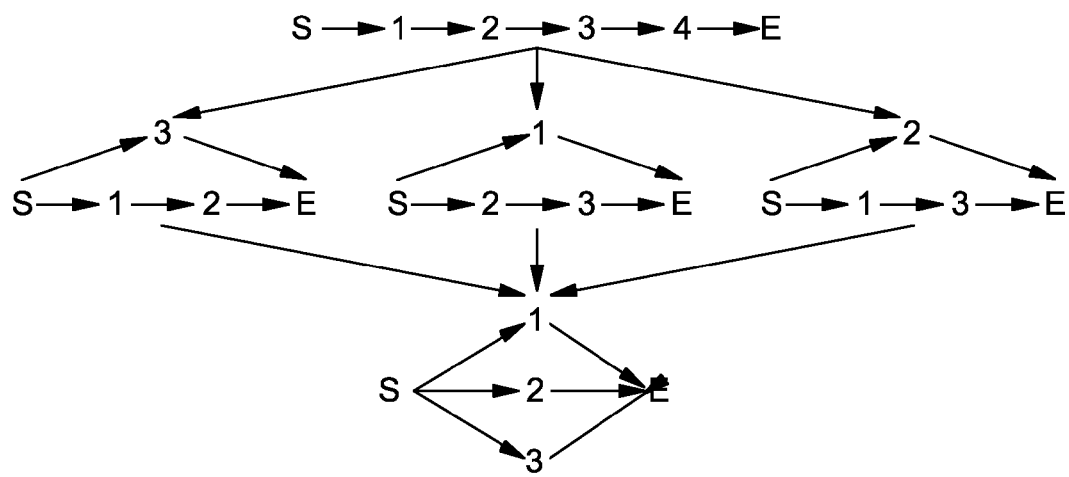
FIG. 9 illustrates five partial orders and the partial order relations among them.

Thus relaxation on d induces a partial order. FIG. 9 shows a small example of the relaxation partial order on partial order descriptors $M_d$'s.

Algorithm for Minimal Descriptions

Figure 10:
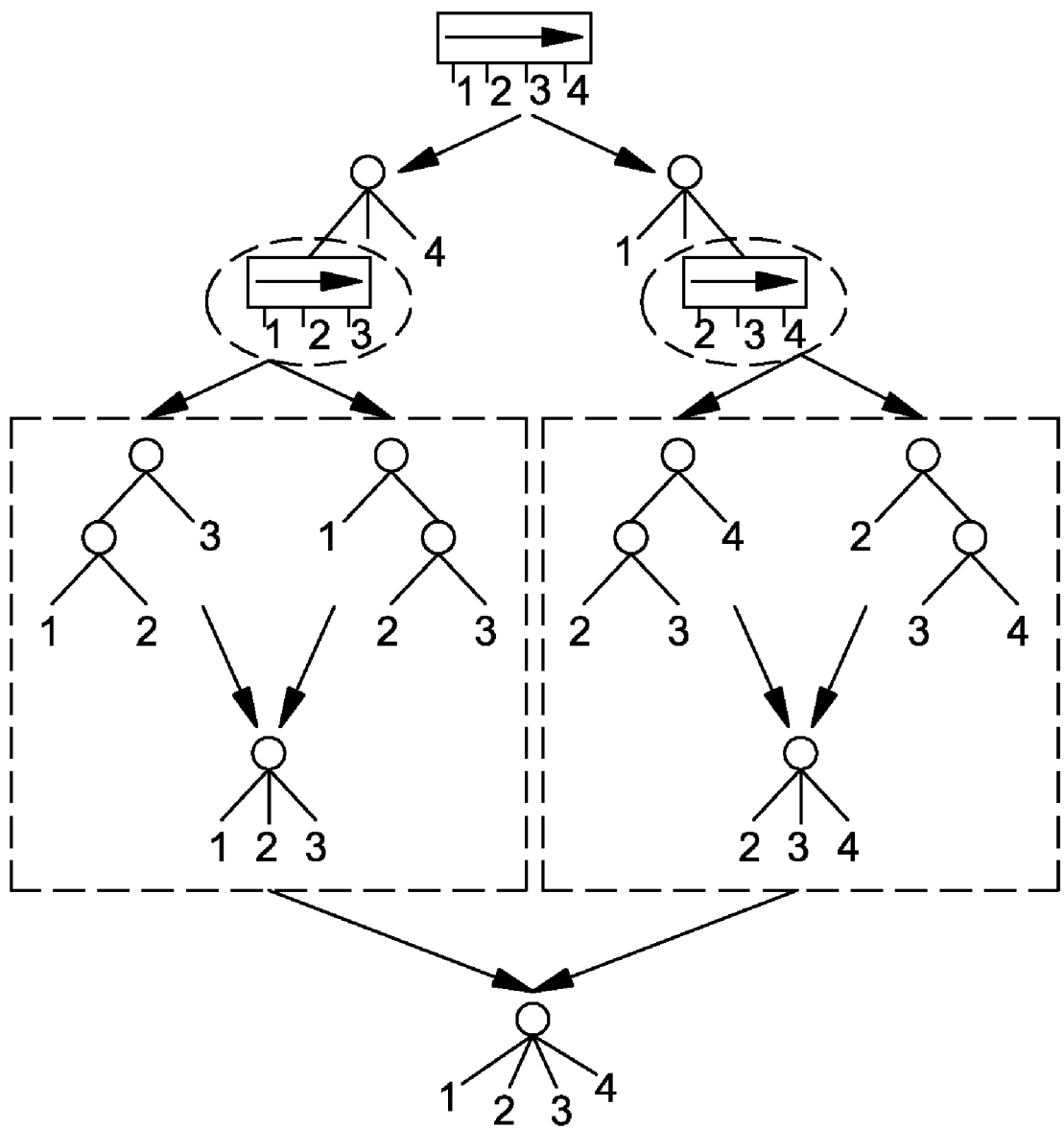
FIG. 10 shows the relaxation of an oPQ structure.

Is there an algorithmic handle on relaxation structures as shown in FIG. 10? Actually, each child $M_c$ of a node M is obtained by the invoking Collapse $(\sigma_1, \sigma_2)$ on M where there is a directed path from $\sigma_1$ to $\sigma_2$ in M. Thus the root node gives three children left to right, corresponding to Collapse(S,3), Collapse(S,1) and Collapse(S,2) respectively. Then Collapse(S,2) on first, Collapse(S,3) on second and Collapse(S,3) on third gives the bottom-most partial order in FIG. 9. Note that this cannot be collapsed any further (without disturbing the roles of S and E).

Note that the partial orders we are using are already augmented by the oPQ structure. However, the oPQ's also admit the partial order structure as shown in FIG. 10.

It is a hierarchical combination of the two (first oPQ and then partial order of each cluster on the oPQ) that gives us the relaxation partial order that we use in the application.

The minimal description can be obtained from this relaxation structures as follows:

Definition 8 (minimal description) Given a data set and the collection of maximal descriptions on it, d' is a minimal description of d if $d' \leq d$ and $O(d)=O(d')$ and there exists no d" with $d'' \leq d'$ and $O(d'')=O(d')$.

The relaxation structure helps in obtaining this minimal description by obtaining the children of a descriptor d in the partial order and then constructing the minimal descriptions.

As will be readily apparent to those skilled in the art, the present invention, or aspects of the invention, can be realized in hardware, software, or a combination of hardware and software. Any kind of computer/server system(s)—or other apparatus adapted for carrying out methods described herein—is suited. A typical combination of hardware and software could be a general-purpose computer system with a computer program that, when loaded and executed, carries out the respective methods described herein. Alternatively, a specific use computer, containing specialized hardware for carrying out one or more of the functional tasks of the invention, could be utilized.

The present invention, or aspects of the invention, can also be embodied in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

While it is apparent that the invention herein disclosed is well calculated to fulfill the objects stated above, it will be appreciated that numerous modifications and embodiments may be devised by those skilled in the art, and it is intended that the appended claims cover all such modifications and embodiments as fall within the true spirit and scope of the present invention.

What is claimed is:

1. A method of using partial order descriptions to identify functions of motifs in a data set, comprising the steps of:
    obtaining the data set, wherein the data set is comprised of a series of data elements;
    identifying a plurality of sequences of motifs in the data set, each of the sequences of motifs comprising a repeating pattern of a plurality of the date elements of the data set;
    for each of the sequences of motifs, identifying a partial order description of the motifs in said each sequence of the motifs; and
    using the identified partial order descriptions of the sequences of motifs to identify functions of the motifs; and
    using a processing unit, implementing a partial order identifying program, to perform the steps of identifying a plurality of sequences of motifs, and identifying a partial order description of the motifs in each sequence of the motifs.

2. A method according to claim 1, wherein the step of identifying the partial order descriptions includes the step of converting the identified motifs to an (n×m) incidence matrix, I, of expressions.

3. A method according to claim 2, wherein the converting step includes the step of using a Boolean expression to compute the expressions of the incidence matrix.

4. A method according to claim 2, wherein the step of identifying the partial order descriptions includes the further step of computing a partial order description of each of said expressions.

5. A method according to claim 4, wherein the step of identifying the partial order descriptions includes the further step of computing a redescription of each of said partial order descriptions.

6. A method according to claim 5, wherein the step of computing a redescription of each of said partial order descriptions includes the step of using all of the partial order descriptions to compute each of the redescriptions.

7. A method according to claim 4, wherein:
    the step of computing a partial order description of each of said expressions includes the step of computing a maximal partial order description of each of said expressions; and
    the step of computing the partial order descriptions includes the further step of computing a minimal form of each of the maximal partial order descriptions.

8. Apparatus for using partial order descriptions to identify functions of motifs in a data set, comprising at least one processing unit configured to (i) obtain the data set, wherein the data set is comprised of a series of data elements, (ii) identify a plurality of sequences of motifs in the data set, each of the sequences of motifs comprising a repeating pattern of a plurality of the data elements of the data set, (iii) for each of the sequences of motifs, identify a partial order description of the motifs in said each sequence of the motifs, and (iv) use the identified partial order descriptions of the sequences of motifs to identify functions of the motifs.

9. Apparatus according to claim 8, wherein the at least one processing unit is configured to convert the identified motifs to an (n×m) incidence matrix, I, of expressions.

10. Apparatus according to claim 8, wherein the at least one processing unit is operative to convert the identified motifs to an (n×M) matrix by using a Boolean expression to compute the expressions of the incidence matrix.

11. Apparatus according to claim 8, wherein the at least one processing unit is configured to compute a partial order description of each of said expressions.

12. Apparatus according to claim 11, wherein the at least one processing unit is configured to compute a redescription of each of said partial order descriptions.

13. Apparatus according to claim 12, wherein the at least one processing unit is configured to use all of the partial order descriptions to compute each of the redescriptions.

14. Apparatus according to claim 11, wherein the at least one processing unit is configured to compute a maximal partial order description of each of said expressions, and to compute a minimal form of each of the maximal partial order descriptions.

15. A program storage device readable by a computer system, tangibly embodying a program of instructions executable by the computer system for using partial order descriptions to identify functions of motifs in a data set, and wherein said computer readable instructions, when executed by the computer system, performs the following:
- obtaining the data set, wherein the data set is comprised of a series of data elements;
- identifying a plurality of sequences of motifs in the data set, each of the sequences of motifs comprising a repeating pattern of a plurality of the data elements of the data set;
- for each of the sequences of motifs, identifying a partial order description of the motifs in said each sequence of the motifs; and
- using the identified partial order descriptions of the sequences of motifs to identify functions of the motifs.

16. A program storage device according to claim 15, wherein the step of identifying the partial order descriptions includes the step of converting the identified motifs to an (n×m) incidence matrix, I, of expressions.

17. A program storage device according to claim 16, wherein the converting step includes the step of using a Boolean expression to compute the expressions of the incidence matrix.

18. A program storage device according to claim 16, wherein the step of identifying the plurality of partial order descriptions includes the further steps of:
- computing a partial order description of each of said expressions; and
- computing a redescription of each of said partial order descriptions.

19. A program storage device according to claim 18, wherein the step of computing a redescription of each of said partial order descriptions includes the step of using all of the partial order descriptions to compute each of the redescriptions.

* * * * *